(12) United States Patent
Muramatsu et al.

(10) Patent No.: US 7,030,396 B2
(45) Date of Patent: Apr. 18, 2006

(54) MEDICAL PARTICLE IRRADIATION APPARATUS

(75) Inventors: Yutaka Muramatsu, Tokai (JP); Hidehito Asano, Ogawa (JP); Wataru Sagawa, Mito (JP); Hiroshi Akiyama, Hitachiohta (JP); Tsutomu Yamashita, Hitachi (JP)

(73) Assignees: Hitachi, Ltd., Tokyo (JP); Hitachi Setsubi Engineering Co., Ltd., Hitachi (JP)

( * ) Notice: Subject to any disclaimer, the term of this patent is extended or adjusted under 35 U.S.C. 154(b) by 0 days.

(21) Appl. No.: 10/724,217

(22) Filed: Dec. 1, 2003

(65) Prior Publication Data

US 2004/0111134 A1 Jun. 10, 2004

Related U.S. Application Data

(62) Division of application No. 10/426,883, filed on May 1, 2003, now Pat. No. 6,803,591.

(30) Foreign Application Priority Data

Sep. 30, 2002 (JP) .............................. 2002-286068

(51) Int. Cl.
  *G21G 5/00* (2006.01)
  *H01J 37/14* (2006.01)
(52) U.S. Cl. ................... 250/492.3; 250/397; 250/398; 250/492.1; 315/502; 315/507; 378/65
(58) Field of Classification Search ............ 250/492.3, 250/397, 398, 492.1; 600/1; 378/17, 65; 315/501, 502, 507
See application file for complete search history.

(56) References Cited

U.S. PATENT DOCUMENTS

| | | | |
|---|---|---|---|
| 5,818,058 A | 10/1998 | Nakanishi et al. | |
| 5,993,373 A | 11/1999 | Nonaka | |
| 6,218,675 B1 | 4/2001 | Akiyama et al. | |
| 6,316,776 B1 | 11/2001 | Hiramoto et al. | |

FOREIGN PATENT DOCUMENTS

| | | |
|---|---|---|
| DE | 19907097 | 8/2000 |
| JP | 11-47287 | 2/1999 |
| JP | 11047287 | 2/1999 |
| JP | 2000-140134 | 5/2000 |
| JP | 2001-129103 | 5/2001 |
| JP | 2001-353228 | 12/2001 |
| JP | 2001353228 | 12/2001 |

*Primary Examiner*—Nikita Wells
*Assistant Examiner*—Paul M. Gurzo
(74) *Attorney, Agent, or Firm*—Dickstein Shapiro Morin & Oshinsky LLP

(57) ABSTRACT

Disclosed is a medical particle irradiation apparatus comprising a rotating gantry 1 including an irradiation unit 4 emitting particle beams; an annular frame 16 located within and supported by the rotating gantry 1 such that it can rotate relative to the rotating gantry 1; an annular frame 15 fixedly located opposite the annular frame 16; an anti-corotation mechanism 34 being in contact with both the annular frames 16 and 15 to prevent the annular frame 16 from rotating together with the rotating gantry 1 during rotation of the rotating gantry 1; and a flexible moving floor 17 interposed between the annular frames 15 and 16, the flexible moving floor 17 being engaged with the annular frames 15 and 16 in such a manner as to move freely such that its bottom is substantially level and that it moves as the rotating gantry rotates.

7 Claims, 9 Drawing Sheets

MEDICAL PARTICLE IRRADIATION APPARATUS

This application is a divisional of U.S. patent application Ser. No. 10/426,883 filed May 1, 2003, which is hereby incorporated by reference now U.S. Pat. No. 6,803,591.

BACKGROUND OF THE INVENTION

1. Field of the Invention

The present invention relates generally to a medical particle irradiation apparatus, and more particularly to a medical particle irradiation apparatus which is suitable for rotating around the patient and irradiating the patient with particle beams from a desired location in the circumferential direction.

2. Description of the Related Art

Particle beams (e.g., proton beam) have captured the spotlight in recent years in radiation therapy (treatment) for cancer as they can treat cancer with relatively small damage to normal cells.

An example of rotary irradiation room for radiation therapy using particle beams is described in Patent Document 1. This rotary irradiation room for radiation therapy has a semicylindrical path with a level bottom formed at each of the fixed and mobile ring rails which are provided opposite each other with the radiation irradiation unit between them, and the flexible moving floor provided within this path is moved in synchronization with the rotation of the radiation irradiation unit. Further, the drive motor provided on the rotating gantry rotates the mobile ring rail in the direction opposite to the radiation irradiation unit's rotation direction by the same amount as the amount of rotation of the radiation irradiation unit. This keeps the positional relationship between the fixed and mobile ring rails which are located opposite each other and allows consistent formation of a level floor used for access to the therapy bed and the radiation irradiation unit even when the rotating gantry rotates.

However, this prior art requires a drive motor for rotating the mobile ring rail in the direction opposite to the rotating gantry's rotation direction and a tilt sensor for detecting the relative positional relationship between the semicylindrical passages formed at the fixed and mobile ring rails and moreover a control unit for controlling them, thus making the configuration complex.

Therefore, an example of rotary irradiation room for particle beam therapy addressing this problem is described in Patent Document 2. This rotary irradiation room for particle beam therapy comprises a fixed shell and fixed shell-side guide rail and rotary shell-side guide rail and activates the locking rod using motor-operated cylinders provided on the fixed shell; this locking rod is engaged with an engagement holes provided on the rotary shell-side guide rail during rotation of the rotating gantry. For this reason, the rotation of the rotary shell-side guide rail is inhibited by the locking rod during rotation of the rotating gantry, thus making it possible to keep the positional relationship between the fixed and rotary shell-side guide rails which are located opposite to each other and keep the bottom of the moving floor constantly level. Two motor-operated cylinders and two engagement holes are provided; the locking rod is pulled out of the engagement hole and reduced in size on the side where the rotation of the particle irradiation unit is hindered while the locking rod is kept in the engagement hole on the side where the rotation is not hindered.

[Patent Document 1]
Japanese Patent Application Laid-open (kokai) Publication No. Hei11-47287

[Patent Document 2]
Japanese Patent Application Laid-open (kokai) Publication No. 2001-129103

Although the drive motor and the tilt sensor in the prior art described in Patent Document 1 are not needed, the prior art described in Patent Document 2 additionally requires locking rods, motor-operated cylinders and a control unit for causing the locking rod to extend or retract with rotation of the particle irradiation unit and attaching and detaching the locking rod, thus resulting in insufficient simplification of the configurations.

SUMMARY OF THE INVENTION

It is therefore the object of the present invention to provide a medical particle irradiation apparatus which ensures more simplified structure and allows formation of the substantially level access floor regardless of the position of the irradiation unit which emits particle beams.

The above object can be achieved by providing an anti-corotation unit which is in contact with both a first frame located within and supported by a rotating gantry such that it can rotate relative to the rotating gantry and a second frame fixedly located opposite the first frame and which prevents the first frame from rotating together with the rotating gantry during rotation of the rotating gantry. Further, the flexible moving floor, interposed between the first and second frames, is engaged with the first and second frames in such a manner as to move freely such that its bottom is substantially level, that it forms therein a particle irradiation room into which a therapy bed is slid and that it moves as the rotating gantry rotates.

Since the anti-corotation unit is in contact with the first frame, located within the rotating gantry such that it can rotate relative to the rotating gantry, and the fixed second frame, the anti-corotation unit which is in contact with the second frame can prevent rotation of the first frame even if the first frame attempts to rotate together with the rotating gantry during rotation of the rotating gantry. Therefore, the positions of the first and second frames which are located opposite each other can be kept substantially unchanged even if the rotating gantry rotates. Consequently, it is possible for the flexible moving floor to form a substantially level access floor regardless of the position of the irradiation unit emitting particle beams.

Moreover, since the anti-corotation unit is located on the rotating gantry, it is moved in the rotating gantry's rotation direction as a result of rotation of the rotating gantry. However, the present invention eliminates the need for the drive motor described in Patent Document 1 which rotates the mobile ring rail in the direction opposite to the rotation direction of the radiation irradiation unit by the same amount as the amount of rotation of the radiation irradiation unit and the drive unit exclusively for the anti-corotation unit, an equivalent of the motor-operated cylinder described in Patent Document 2 which moves the locking rod. The present invention does not require any exclusive drive unit for the anti-corotation unit and any control unit for this drive unit, thus allowing simplification of the structure.

It is also possible to dispose the anti-corotation unit on the irradiation unit which rotates together with the rotating gantry during rotation of the rotating gantry and emits particle beams. Disposition of the anti-corotation unit on the irradiation unit means that the anti-corotation unit lies on the rotating gantry although it is not directly disposed on the rotating gantry.

BRIEF DESCRIPTION OF THE DRAWINGS

The above and other objects, aspects, features and advantages of the present invention will become more apparent from the following detailed description when taken in conjunction with the accompanying drawings, in which.

DESCRIPTION OF THE PREFERRED EMBODIMENT

An embodiment of the present invention will now be described with reference to the drawings.

Figure 1:
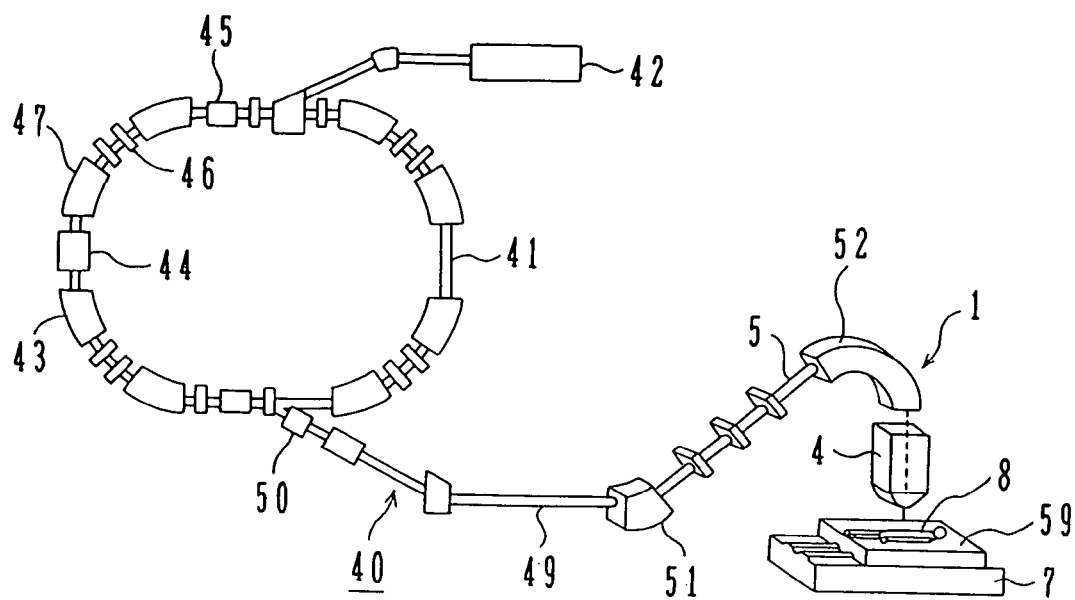
FIG. 1 illustrates the schematic configuration of a medical particle irradiation apparatus which is a preferred embodiment of the present invention.
Figure 2:
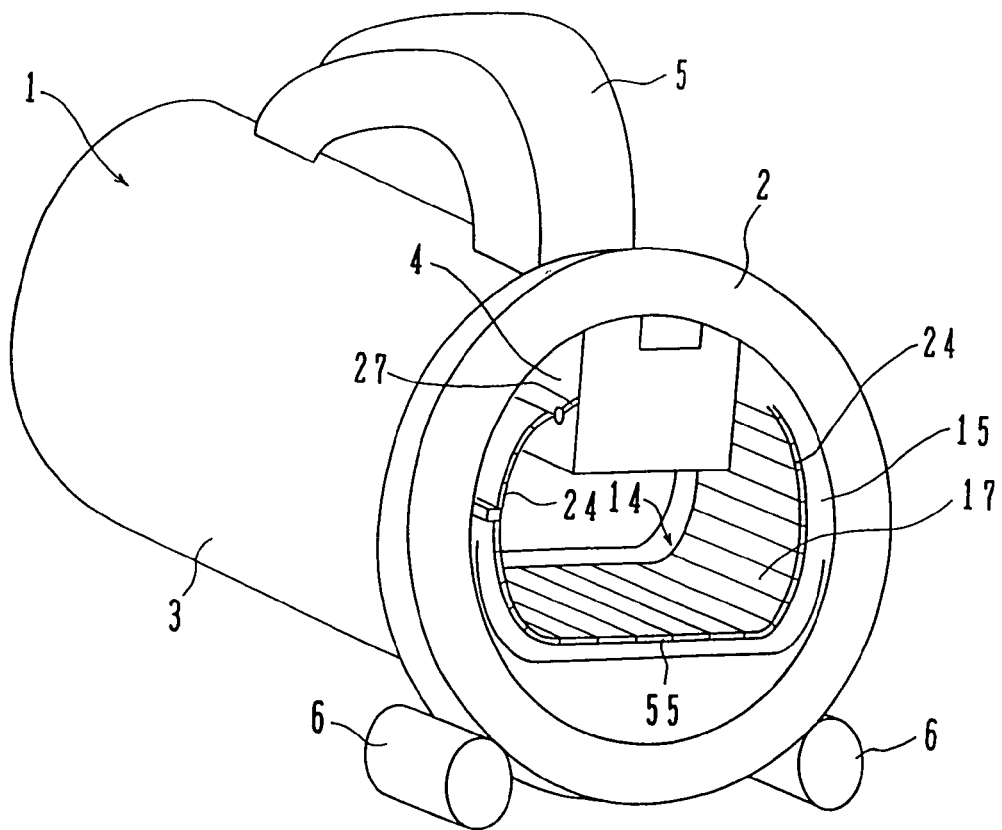
FIG. 2 is a perspective view of a rotating gantry employed in the medical particle irradiation apparatus of FIG. 1.

A medical particle irradiation apparatus of this embodiment is described referring to FIGS. 1 and 2. The medical particle irradiation apparatus of this embodiment is designated at 40 and comprises a charged particle beam generating unit 41 and a rotating gantry 1. The charged particle beam generating unit (particle beam generating unit) 41 has an ion source not shown, a preaccelerator 42 and a synchrotron 43. Ions generated in the ion source (e.g., proton ions (or carbon ions)) are accelerated by the preaccelerator 42 (e.g., linear accelerator). The ion beam emitted by the preaccelerator 42 enters the synchrotron 43. That beam which is a charged particle beam (particle beam) is accelerated in the synchrotron 43 as it is given energy by radio-frequency power applied by a radio frequency accelerating cavity 44. After the energy of the ion beam orbiting within the synchrotron 43 is raised to the preset energy (normally 100 to 200 MeV), radio frequency is applied to the ion beam by a radio frequency application unit for emission 45. The ion beam orbiting within the stability limit moves outside the stability limit as a result of this radio frequency application, passes through an emission deflector 50 and is emitted from the synchrotron 43. At the time of ion beam emission, currents introduced into electromagnets such as a quadrupole electromagnet 46 and a polarized electromagnet 47 are kept at the preset value, with the stability limit kept nearly constant. Stopping the radio frequency application unit 45 from applying radio frequency allows ion beam emission from the synchrotron 43 to be stopped.

The ion beam emitted by the synchrotron 43 reaches a particle irradiation unit (irradiation nozzle) 4 via a beam transfer system 49. The affected area (cancer-affected area) of a patient 8 on a therapy bed 59 is irradiated with the ion beam from the particle irradiation unit 4. The particle irradiation unit 4 generates ion beam which forms an optimal dos distribution for particle beam therapy.

Figure 3:
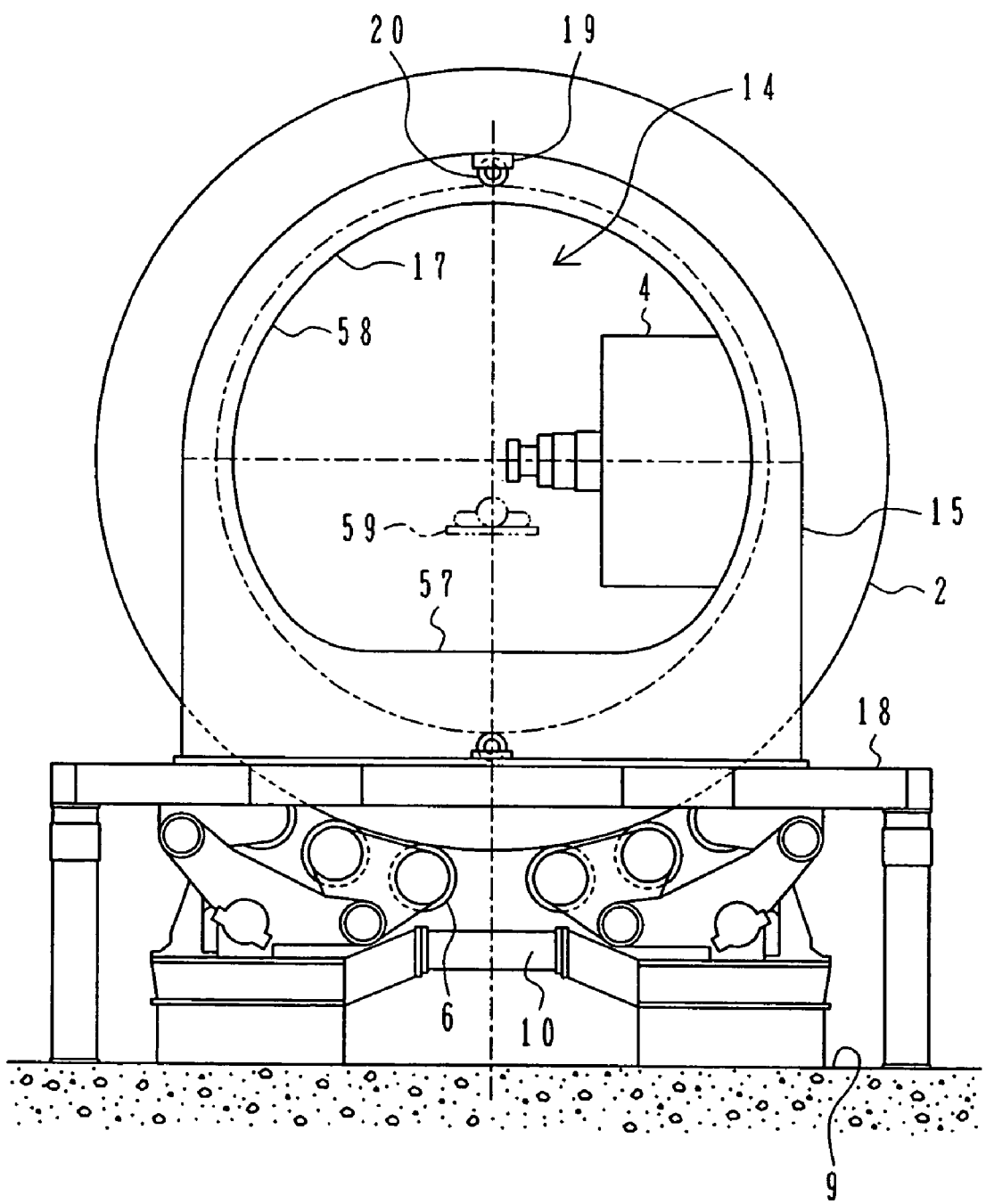
FIG. 3 is a transverse sectional view, showing the sectional structure of an irradiation room for particle beam therapy disposed in the rotating gantry of FIG. 2, FIG. 3 being a sectional view taken along line IV—IV of FIG. 5.

The rotating gantry 1 comprises a rotary shell (rotational element) 3 in substantially cylindrical form having a front ring 2 and a motor (rotation unit) not shown for rotating the rotary shell 3. The front ring 2 provided at one end of the rotary shell 3 is supported by a plurality of rotatable support rollers 6. These support rollers 6 are attached to a support unit 10, which is disposed in a rotating gantry disposition area (building foundation) 9, such that they are free to rotate as shown in FIG. 3. Although not shown, the other ring (whose outer diameter is equal to that of the front ring 2) provided at the other end of the rotary shell 3 is supported by a plurality of the support rollers 6 attached to the other support unit 10 such that they are free to rotate. A reverse U-shaped beam transfer unit 5, which is part of the beam transfer system 49, and the particle irradiation unit 4 are provided on the rotary shell 3 and rotate as the rotating gantry 1 rotates. The beam transfer unit 5 has electromagnets such as polarized electromagnets 51 and 52. A therapy gauge (therapy room) 14 is formed within the rotary shell 3.

The medical particle irradiation apparatus 40 has an irradiation room for particle beam therapy 55 provided within the rotary shell 3 of the rotating gantry 1. The detailed structure of the irradiation room for particle beam therapy 55 is described by referring to FIGS. 4 and 5. The irradiation room for particle beam therapy 55 comprises a fixed annular frame (ring member) 15, an annular frame 16, a moving floor 17 and an anti-corotation mechanism (frame position retaining unit, position retaining unit) 34.

The annular frame 15 is provided on the front ring 2 side of the rotary shell 3 and secured to a base 18 disposed in the rotating gantry disposition area 9. The annular frame 16 is provided on the other side of the rotary shell 3 and located across a path of the particle irradiation unit 4 from the annular frame 15. The annular frame 16 is supported by a plurality of support rollers 20 attached to a support frame 19, which is secured to the inner surface of the rotary shell 3, such that they are free to rotate. That is, the annular frame 16 is free to rotate relative to the rotating gantry by the support rollers 20. The annular frames 15 and 16 comprise on their respective opposed sides ring guide portions 15A and 16A in which guide grooves with level bottom and circular top are formed. The guide grooves are semicylindrical in shape as a result of their level and circular portions.

Figure 6:
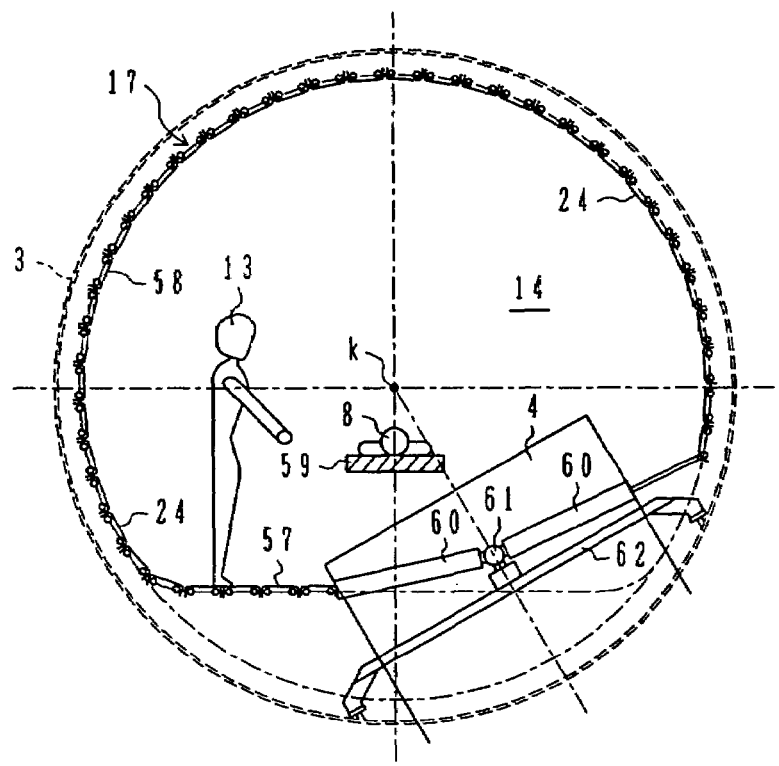
FIG. 6 is a sectional view taken along line V—V of FIG. 4.

The moving floor 17, as shown in FIG. 6, has a flexible structure with a number of plates 24 in which the adjacent plates 24 are connected to each other with links not shown. Each of the plates 24 is arranged such that it faces the center of rotation of the rotating gantry 1. The moving floor 17 possesses sufficient stiffness to defy deformation even when a doctor or others 13 works on top of it. One end of the moving floor 17 is engaged with the guide groove of the ring guide portion 15A while the other end with the guide groove of the ring guide portion 16A. The structure of that engagement condition is described using FIG. 7. Each of the plates 24 is slightly shorter than the distance between the opposed sides of the ring guide portions 15A and 16A. A wheel 25 is attached to each end of the plates 24. Each of the wheels 25 located at the end on the annular frame 16 side of each of the plates 24 is slid into a guide groove 56 formed on the ring guide portion 16A. Although not shown, each of the wheels 25 located at the end on the annular frame 15 side of each of the plates 24 is slid into the guide groove 56 formed on the ring guide portion 15A. Further, a side wheel 26 which rotates while being in contact with the side of the ring guide portion 16A is provided at the end on the annular frame 16 side of each of the plates 24. Although not shown, the side wheel 26 which rotates while being in contact with the side of the ring guide portion 15A is provided at the end on the annular frame 15 side of each of the plates 24.

Moreover, each of the circumferential ends of the moving floor 17 is coupled to the particle irradiation unit 4 via a telescopic cylinder 60 and a pin 61, with the pin 61 attached to the particle irradiation unit 4 to couple the cylinder 60 so as to allow its free rotational movement. Additionally, the pin 61 is also supported by the rotary shell 3 via a support base member 62. This makes it possible to control the circumferential position of the moving floor 17 through extension or retraction (OUT/IN of the rod portion) of the cylinder 60.

If the rotating gantry 1 rotates as it is driven by a motor, the particle irradiation unit 4 moves in that rotation direction. The moving floor 17 which is coupled to the particle irradiation unit 4 by the pin 61 and the cylinder 60 also moves in that rotation direction as it is pulled by the cylinder 60 coupled to the particle irradiation unit 4. Movement of the moving floor 17 is carried out smoothly along the respective guide grooves 56 of the ring guide portions 15A and 16A since the wheels 25 are provided for each of the plates 24. Movement of the moving floor 17 along the circular portion and from the level to circular portions (or from the circular to level portions) of each of the guide grooves 56 is also carried out smoothly since the moving floor 17 couples the adjacent plates 24 with links not shown so as to be flexible.

Figure 4:
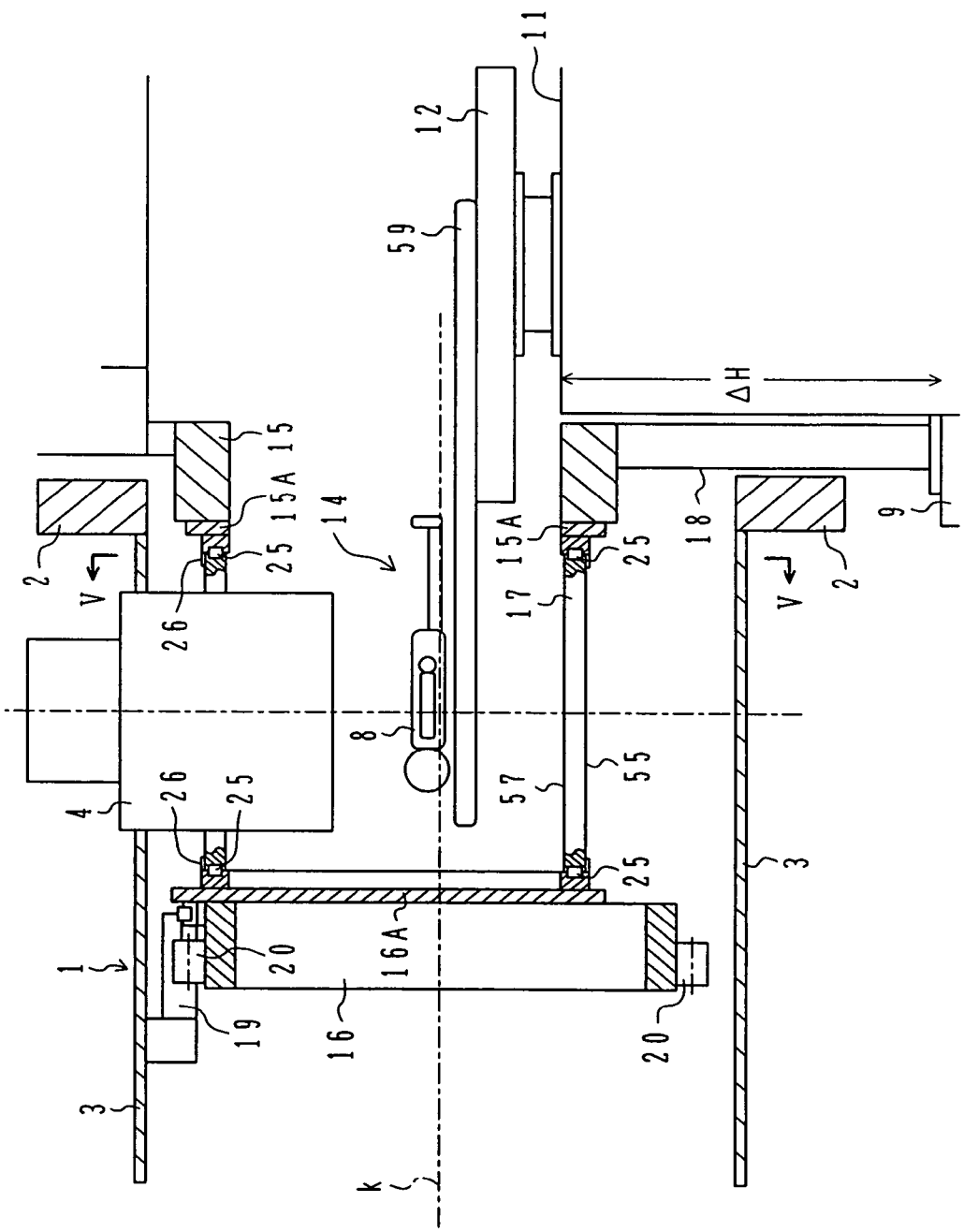
FIG. 4 is a conceptual longitudinal sectional view showing the overall schematic structure of the irradiation room for particle beam therapy disposed in the rotating gantry shown in FIG. 2.

The moving floor 17, engaged with the ring guide portions 15A and 16A, forms a level floor portion 57 at the bottom of the annular frames 15 and 16 by the level portion of each of the guide grooves 56 and a circular wall portion 58 at the top of the annular frames 15 and 16 by the circular portion of each of the guide grooves 56. The therapy gauge 14 is formed inside the moving floor 17. The therapy bed 59 is slid into the therapy gauge 14 when ion beam is emitted from the particle irradiation unit 4. A therapy stage 7 equipped with the therapy bed is disposed on top of a therapy stage disposition area 11 which is one step higher than the rotating gantry disposition area 9, as shown in FIG. 4. The therapy stage 7 is attached. The therapy stage 7 further comprises a drive unit (bed drive means) 12. The therapy bed 59 is moved by the drive unit (bed drive means) 12 and slid into and out of the therapy gauge 14. When the therapy bed 59 is in the therapy gauge 14, the position of the therapy bed 59 along its height is adjusted by the drive unit 12 such that the patient 8 on the therapy bed 59 or on the therapy stage 7 is at a center of rotation k of the rotating gantry 1. Further, the therapy bed 59 is positioned by the drive unit 12 such that the affected area (position to be irradiated with ion beam) of the patient 8 is on the line extended from the axis of the particle irradiation unit 4. This allows irradiation of the affected area of the patient 8 with ion beam emitted from the particle irradiation unit 4. Since the moving floor 17 is moved in the direction in which the particle irradiation unit 4 moves as a result of the rotation of the rotating gantry 1, it is possible to irradiate the affected area of the patient 8 with ion beam from 360-degree range in the circumferential direction of the rotary shell 3.

The floor level of the rotating gantry disposition area 9 is one step lower to secure a rotation radius of the rotating gantry 1. In contrast, the level of the therapy stage disposition area 11's top surface is nearly the same as that of the level floor portion 57's top surface in consideration of access of the doctor 13 (or medical technologist, nurse) to the level floor portion 57. For this reason, a difference in height ΔH (FIGS. 1 and 2) between the top surfaces of the rotating gantry disposition area 9 and the therapy stage disposition area 11 is normally 6 to 8 m. Since the level floor portion 57 is formed, it is possible for the doctor or others 13 to readily and safely engage in medical practice for the patient 8 on the therapy bed 59, which is slid into the therapy gauge 14, at a height 6 to 8 m above the rotating gantry disposition area 9 before and after ion beam irradiation by entering the therapy gauge 14.

The moving floor 17, engaged with the ring guide portions 15A and 16A, forms the level floor portion 57 which serves as scaffolding for the doctor 13 (or medical technologist and so on) to work and forms the therapy gauge 14 which provides a closed space from surrounding areas. Formation of the therapy gauge 14, which is a closed space, prevents the patient 8 on the therapy bed 59 from having fear due to height.

The cylinder 60 attached to the moving floor 17 is a drive cylinder disclosed in Japanese Patent Application Laid-open (kokai) Publication No. 2001-353228. The drive cylinder is controlled to extend or retract according to the rotation angle of the particle irradiation unit 4 (in other words, rotation angle of the rotating gantry 1). Therefore, the moving floor 17 is never short despite its reduction in size regardless of the rotation angle by which the particle irradiation unit 4 moves, thus reliably securing the level floor portion 57 serving as scaffolding near the therapy bed 59.

Figure 5:
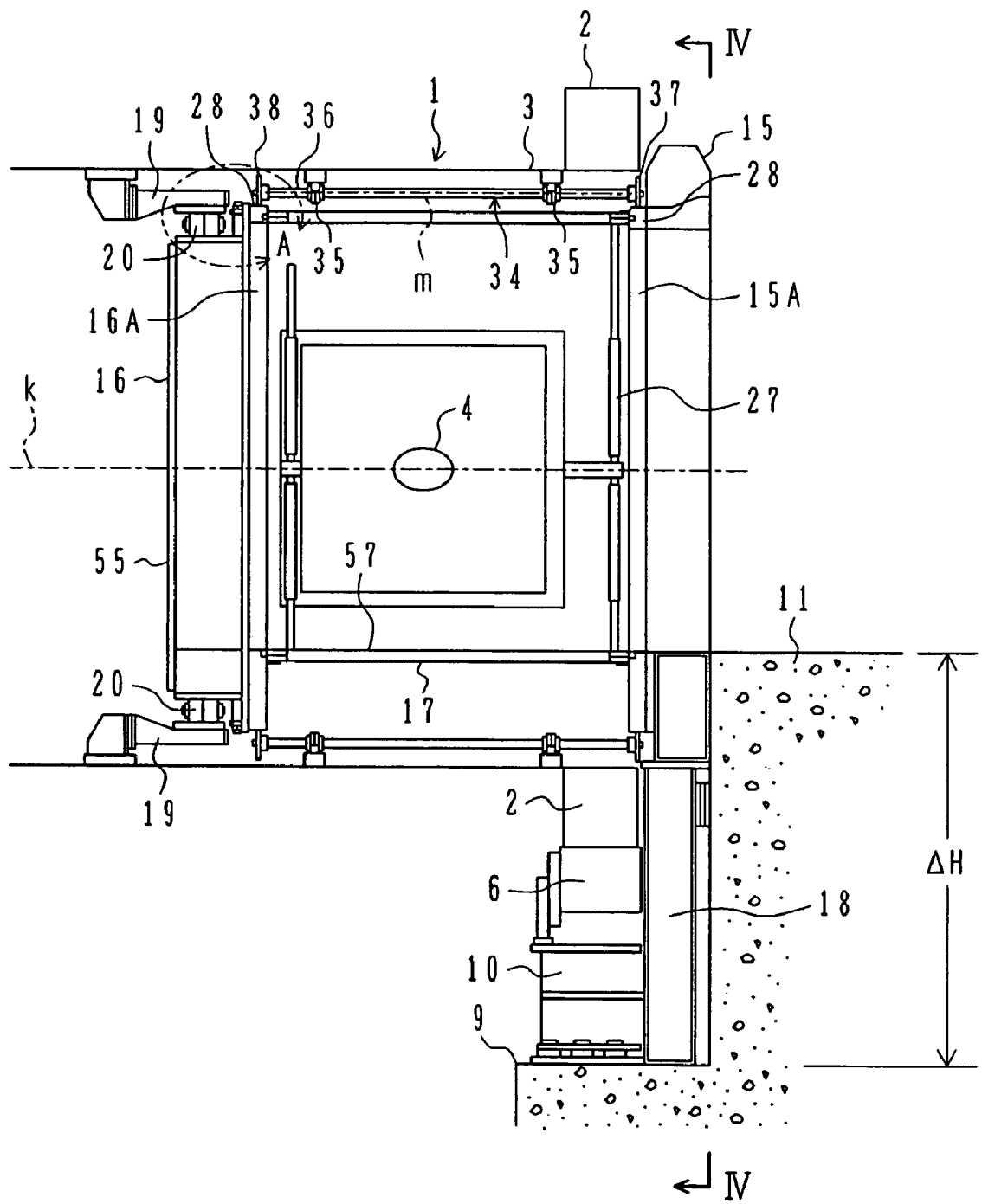
FIG. 5 is a longitudinal sectional view showing the detailed structure of major portions of the irradiation room for particle beam therapy shown in FIG. 4.
Figure 7:
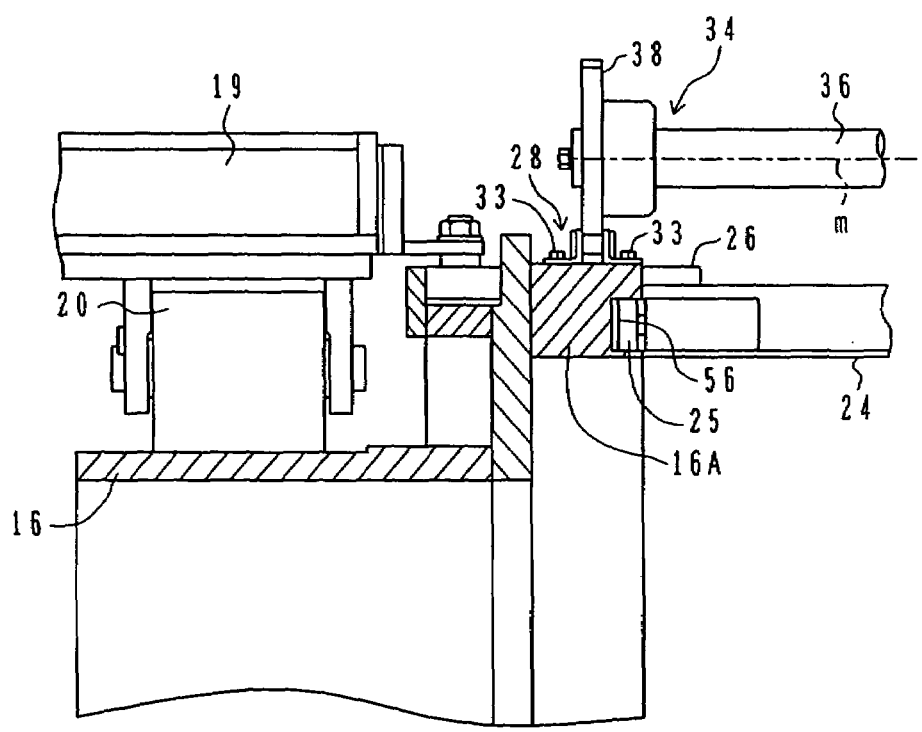
FIG. 7 is an enlarged sectional view of portion A of FIG. 5, showing the support structure at both ends of a moving floor.

The prime feature of this embodiment is provision of the anti-corotation mechanism 34 which rotates on its axis while being engaged (in contact) with the respective outer radius portions of the annular frames 15 and 16 during rotation of the rotating gantry 1 and keeps the positions of the annular frames 15 and 16 positioned opposite each other substantially unchanged by revolving together with the rotating gantry 1. The anti-corotation mechanism 34 has a connecting shaft (shaft member) 36 attached to bearings 35 disposed on the inner surface of the rotating gantry 1's rotary shell such that it is free to rotate (rotate on its axis) and sprockets 37 and 38 which are rotational elements, each attached to one end of the connecting shaft 36, as shown in FIGS. 5 and 7. The anti-corotation mechanism 34 is disposed at least at one location (preferably at several locations), for example, in the circumferential direction of the rotary shell 3. The anti-corotation mechanism 34 is disposed in the circumferential direction of the rotary shell 3, at a distance from the particle irradiation unit 4 and on the inner surface of the rotary shell 3 such that it is rotatable.

Figure 8A:
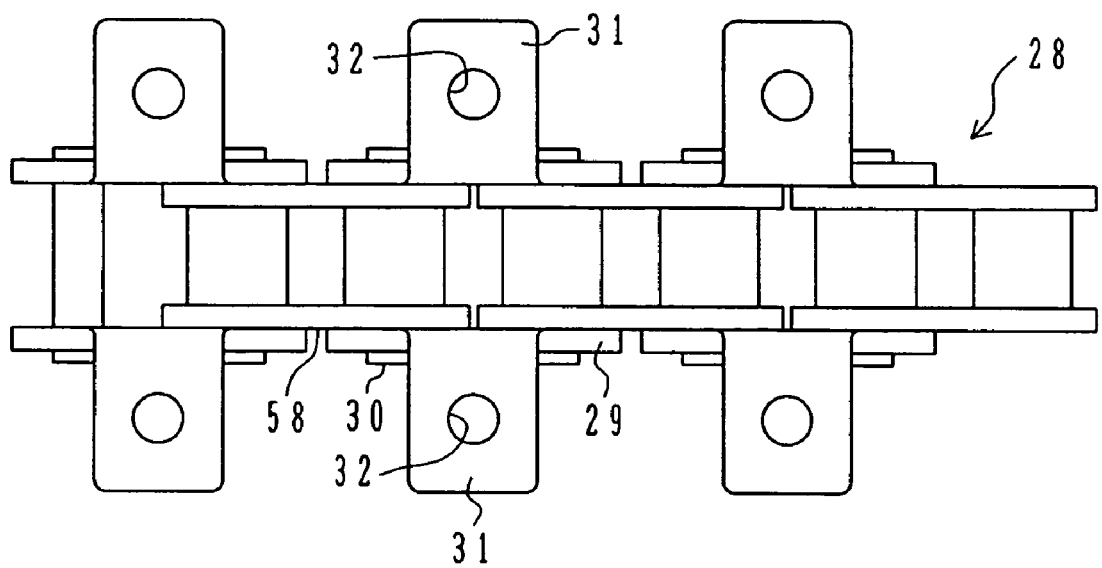
FIGS. 8A and 8B illustrate the structure of a conveyor chain shown in FIG. 7, with FIGS. 8A and 8B being a top plan view and a side view, respectively, of the conveyor chain.
Figure 8B:
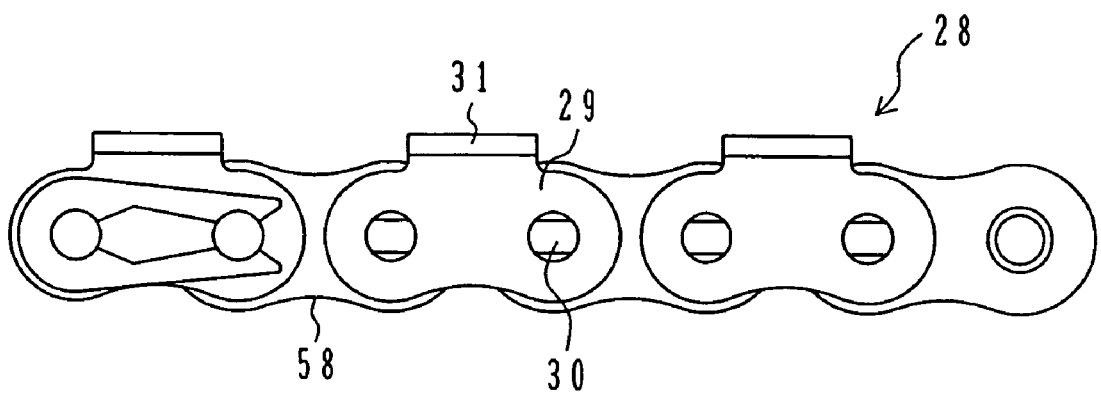
Figure 9:
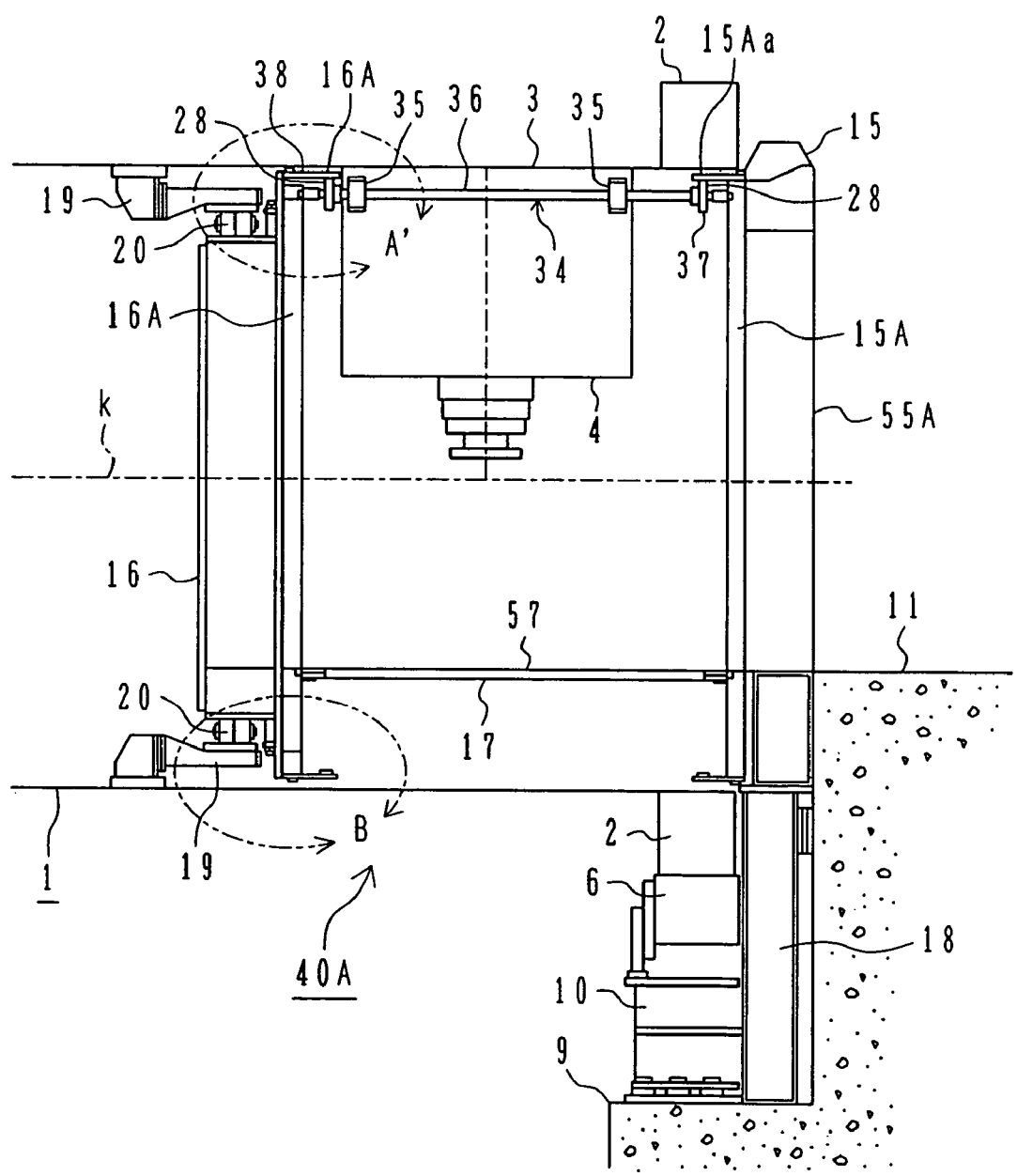
FIG. 9 is a longitudinal sectional view showing the detailed structure of major portions of the irradiation room for particle beam therapy employed in the medical particle irradiation apparatus which is another embodiment of the present invention.
Figure 10:
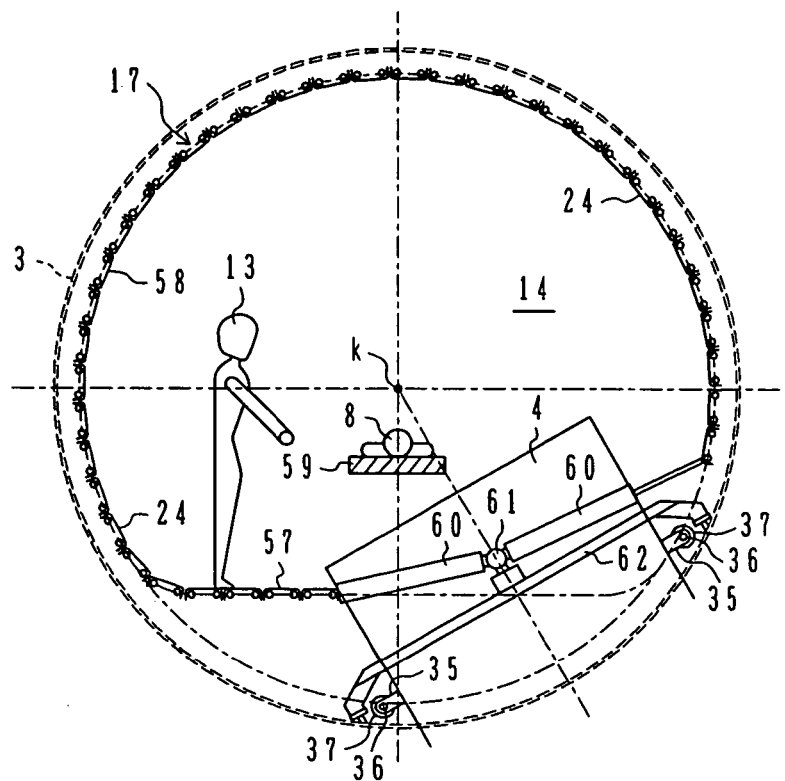
FIG. 10 is a transverse sectional view of the irradiation room for particle beam therapy of FIG. 9.

Conveyor chains (endless links) 28 serving as uneven portions are attached to the outer radial surfaces of the ring guide portions 15A and 16A. The detailed structure of the conveyor chains 28 is shown in FIGS. 8A and 8B. Each of the conveyor chains 28 is formed into endless configuration by arranging a number of link members 29 and link members 59 alternately and connecting them with pins 30 through articulated connection such that they are free to move rotationally. Each of the link members 29 is provided with a bracket portion 31 having a bolt hole 32 on each side. The link members 29 are disposed on the outer radial surface of the ring guide portion 16A by attaching fixing bolts 33, threaded through the bolt holes 32, to the outer radius portion of the ring guide portion 16A. When all the link members 29 are disposed on the outer radial surface of the ring guide portion 16A, one of the conveyor chains 28 is disposed on the outer radial surface of the ring guide portion 16A as shown in FIG. 7. The other conveyor chain 28 is similarly disposed on the outer radial-surface of the ring guide portion 15A.

The sprocket 37 of the anti-corotation mechanism 34 meshes with the conveyor chain 28 disposed on the outer radial surface of the ring guide portion 15A. The other sprocket 38 of the anti-corotation mechanism 34 meshes with the conveyor chain 28 disposed on the outer radial surface of the ring guide portion 16A. In other words, the sprocket 37 is in contact with the conveyor chain 28 disposed on the ring guide portion 15A while the sprocket 38 with the conveyor chain 28 disposed on the ring guide portion 16A.

The sprockets 37 and 38 both have the same numbers of teeth, with their tooth pitches being equal. The conveyor chains 28 disposed respectively on the ring guide portions 15A and 16A both have the same numbers of the link members 29 and 59, with the pin 30 pitches being equal. A center of rotation m of the connecting shaft 36 (axis of the sprocket 37 or 38) is parallel with the center of rotation k of the rotating gantry 1 (=axis of the annular frame 15 or 16). In other words, the distance from the axis of the sprocket 37 to the axis of the annular frame 15 is equal to the distance from the axis of the sprocket 38 to the axis of the annular frame 16. This allows the anti-corotation mechanism 34 to function as a position retaining unit which keeps the positions of the annular frames 15 and 16, which are located opposite each other, substantially constant.

In this embodiment, one of the conveyor chains 28 is indirectly attached to the annular frame 15 via the ring guide portion 15A while the other indirectly attached to the annular frame 16 via the ring guide portion 16A. However, one of the conveyor chains 28 may be directly attached to the outer radial surface of the annular frame 15 on which the guide groove 56 is formed while the other conveyor chain 28 attached directly to the outer radial surface of the annular frame 16 on which the guide groove 56 is form d. Such indirect and direct attachment structures are both none other than formation of mating portions on the annular frames 15 and 16 which mesh with a pair of rotational elements provided on the anti-corotation mechanism 34.

Next, the operation and functions of this embodiment are described.

The rotating gantry 1 is allowed to rotate by driving a rotating gantry motor. The rotating gantry 1 stops rotating when the ion beam irradiation direction, determined in the therapy program for the patient 8, agrees with the axis of the particle irradiation unit 4. Then the therapy bed 59, on which the patient 8 lies, is slid into the therapy gauge 14 to perform positioning such that the affected area of the patient 8 is on the line extended from the axis of the particle irradiation unit 4.

When the rotating gantry 1 rotates, the rotary shell 3 rotates. Since the annular frame 16 is held via the support rollers 20 such that it is free to rotate, the annular frame 16 also attempts to rotate with rotation of the rotary shell 3 as a result of friction and so on generated by the support rollers 20 and so on. This phenomenon is referred to as corotation. Note that since the moving floor 17 also moves within the guide groove 56 of the ring guide portion 16A as a result of movement of the particle irradiation unit 4 associated with rotation of the rotary shell 3, corotation of the annular frame 16 may further intensify due to contact friction and so on of the moving floor 17 which moves. However, corotation does not take place with the annular frame 15 since it is secured to the base 18.

Since the anti-corotation mechanism 34 is provided in this embodiment, the annular frame 16 is prevented from rotating together with the rotating gantry when the rotating gantry 1 rotates. The reason for this is described below.

The anti-corotation mechanism 34 is attached to the rotary shell 3 via the bearings 35, and since the sprockets 37 and 38 mesh with the conveyor chains 28 disposed respectively on the ring guide portions 15A and 16A, the anti-corotation mechanism 34 moves in the rotation direction of the rotary shell 3 (movement direction of the particle irradiation unit 4) while rotating on its axis as the rotary shell 3 rotates. Movement of the anti-corotation mechanism 34 in the rotation direction of the rotary shell 3 (movement direction of the particle irradiation unit 4) is revolution of the anti-corotation mechanism 34 along the outer radius portions of the ring guide portions 15A and 16A.

Since the sprocket 37 meshes with the conveyor chain 28 provided on the fixed ring guide portion 15A, the sprocket 38 which is secured to the sprocket 37 by the connecting shaft 36 prevents the ring guide portion 16A, that is, the annular frame 16 from rotating during revolution of the anti-corotation mechanism 34 by mating with the conveyor chain 28 provided on the ring guide portion 16A. The capability of the anti-corotation mechanism 34 to prevent the annular frame 16 from rotating is activated throughout revolution of the anti-corotation mechanism 34. Therefore, the annular frame 16 does not rotate and always stands still even when the rotating gantry 1 rotates. In this embodiment, the positions of the annular frames 15 and 16 located opposite each other remain substantially unchanged even when the rotary shell 3, that is, the rotating gantry 1 rotates. Although rotation of the rotating gantry 1 results in movement of the moving floor 17 along the guide grooves 56 of the ring guide portions 15A and 16A, the level floor portion 57 is kept substantially level at all times below the annular frames 15 and 16 in this embodiment since the positions of the annular frames 15 and 16 located opposite each other remain substantially unchanged.

This makes it possible to secure work space for safe engagement in medical practice by the doctor 13 or others by the level floor portion 57 formed near the therapy bed 59 which is slid into the therapy gauge 14.

As mentioned earlier, since the annular frame 16 is attached to the rotary shell 3 by the support rollers 6 such that it can rotate relative to the rotary shell 3, the rotary shell 3, that is, the rotating gantry 1 can rotate around the annular frame 16 even if the annular frame 16 substantially always stands still.

If the above-mentioned corotation takes place with the annular frame 16, the positions of the annular frames 15 and 16 located opposite each other change, possibly damaging the moving floor 17 due to torsional force and preventing the level portion of the moving floor 17 from being formed under the ring guide portion 16A. The medical particle irradiation apparatus 40 equipped with the anti-corotation mechanism 34 does not present such a problem.

Since the connecting shaft 36 is supported by the inner surface of the rotary shell 3 via a pair of the bearings 35, the anti-corotation mechanism 34 is moved in the rotation direction of the rotary shell 3 in synchronization with the rotation of the rotary shell 3 and the position of contact between the sprocket 38 and the annular frame 16, more specifically, the position of contact between the sprocket 38 and the conveyor chain 28 disposed on the outer radial surface of the annular frame 16 moves in that rotation direction in succession when rotation of the annular frame 16 is prevented as mentioned earlier. The anti-corotation mechanism 34 and the particle irradiation unit 4 move in that rotation direction as the rotary shell 3 rotates while keeping the preset distance between them constant in the circumferential direction of the rotary shell 3. In Patent Document 2, since the particle irradiation unit interferes with the locking rod as a result of movement of the rotating gantry, it is necessary to extend or retract the locking rod. With this embodiment, movement of the particle irradiation unit 4 is never hindered by the anti-corotation mechanism 34.

This embodiment eliminates the need for the drive motor described in Patent Document 1 which rotates the mobile ring rail in the direction opposite to the rotation direction of the radiation irradiation unit by the same amount as the amount of rotation of the radiation irradiation unit and the drive unit exclusively for the anti-corotation mechanism, an equivalent of the motor-operated cylinder described in Patent Document 2 which moves the locking rod. Moreover, the control unit for the drive unit is not required. With this embodiment, it is possible to prevent the annular frame 16 from rotating together with the rotating gantry 1 using simple configurations not requiring the drive unit exclusively for the anti-corotation mechanism such as disposition of a pair of the sprockets 37 and 38 coupled with the connecting shaft 36 on the rotating gantry 1 and disposition of the conveyor chains on the annular frames 15 and 16. This ensures simplified configurations of the irradiation room for particle beam therapy 55, eventually allowing simplified configurations of the medical particle irradiation apparatus 40.

This embodiment essentially adopts a structure in which rotation of the annular frame 16, disposed such that it can rotate relative to the rotating gantry 1, is prevented by the member engaged with the fixed annular frame 15. Since the member restrains 360-degree movement of the particle irradiation unit 4 in the circumferential direction of the rotary shell 3 with this structure, this embodiment has adopted a configuration which allows the member to move in the rotation direction of the rotating gantry 1 together with the particle irradiation unit 4 by installing that member on the rotary shell 3, that is, the rotating gantry 1.

The medical particle irradiation apparatus according to another embodiment of the present invention is described with reference to FIGS. 9, 10, 11 and 12. A medical particle irradiation apparatus 40A of this embodiment has configurations in which the irradiation room for particle beam therapy 55 of the medical particle irradiation apparatus 40 in the embodiment is replaced with an irradiation room for particle beam therapy 55A. Of the configurations of the irradiation room for particle beam therapy 55A, those which are the same as the configurations of the irradiation room for particle beam therapy 55 are assigned the identical signs. The portions which are different from the configurations of the irradiation room for particle beam therapy 55 are described.

Figure 11:
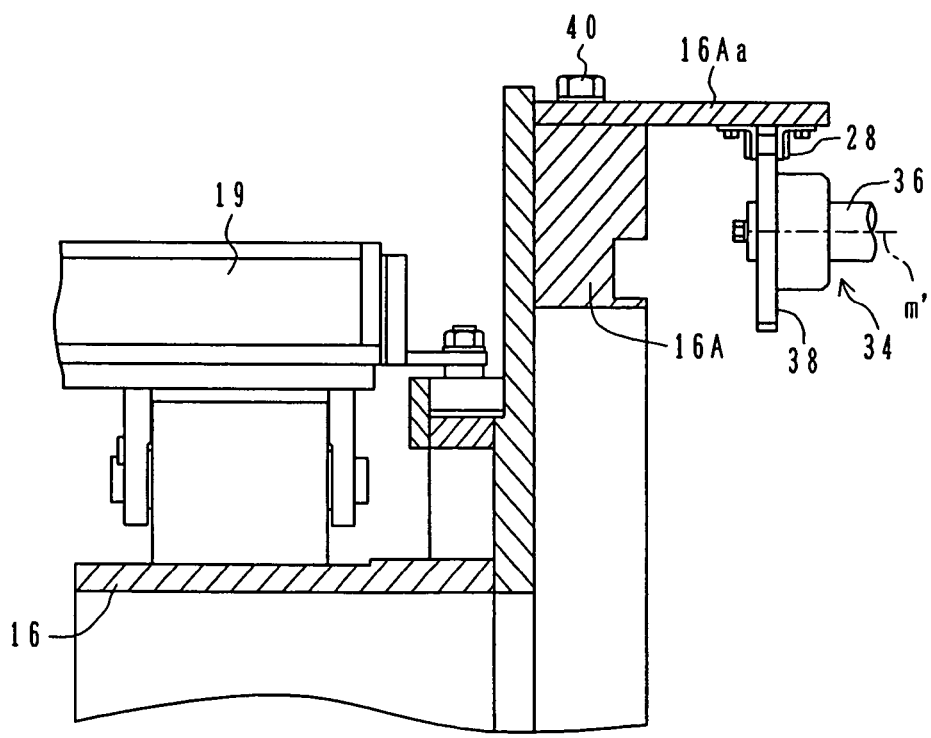
FIG. 11 is an enlarged sectional view of portion A' of FIG. 9, showing the support structure at both ends of an anti-corotation mechanism.
Figure 12:
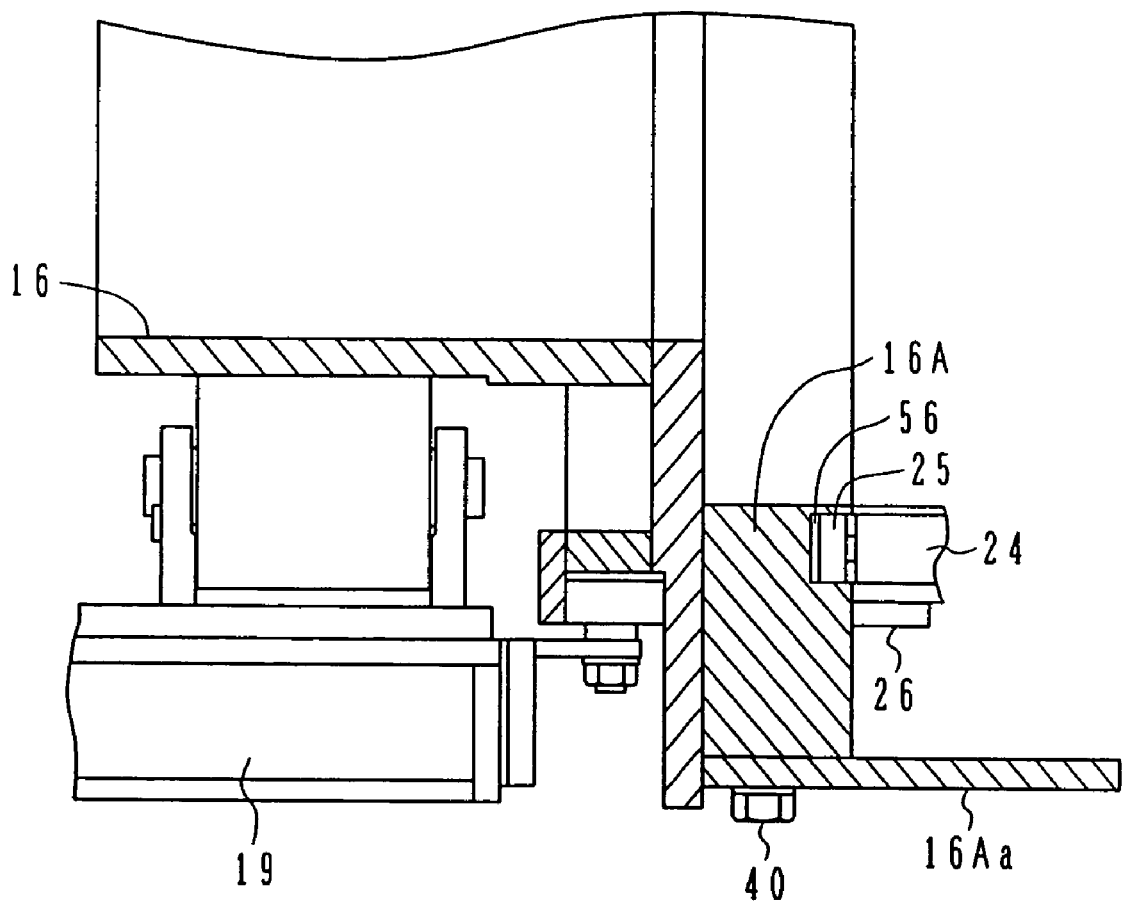
FIG. 12 is an enlarged sectional view of portion B' of FIG. 9, showing the support structure at both ends of the moving floor.

With the irradiation room for partial beam therapy 55A, a cylindrical chain attachment portion 16Aa is attached to the outer radial surface of the ring guide portion 16A with a bolt 40 (FIGS. 11 and 12). The conveyor chain 28 is attached to the inner radial surface of the chain attachment portion 16Aa. Attachment of the conveyor chain 28 to that inner radial surface is conducted using the bracket portion 31 as with the irradiation room for particle beam therapy 55. The conveyor chain 28 is attached to the ring guide portion 15A by attaching the conveyor chain 28 to the inner radial surface of a cylindrical chain attachment portion 15Aa provided on the outer radial surface of the ring guide portion 15A as with the ring guide portion 16A.

The anti-corotation mechanism 34 has a pair of the sprockets 37 and 38 coupled with the connecting shaft 36 and is provided on the inside of the rotary shell 3 (more specifically, the connecting shaft 36 is supported by a pair of the bearings 35, which are secured to the particle irradiation unit 4, such that it is free to rotate (rotate on its axis) as shown in FIG. 1). The sprocket 37 of the anti-corotation mechanism 34 meshes with the conveyor chain 28 of the chain attachment portion 15Aa while the sprocket 38 with the conveyor chain 28 of the chain attachment portion 16Aa. A center of rotation m' of the connecting shaft 36 (axis of the sprocket 37 or 38) is substantially parallel with the center of rotation k of the rotary shell 3 (=axis of the fixed frame 15 or the rotary frame 16). That is, the distance from the axis of the sprocket 37 to the axis of the annular frame 15 is equal to the distance from the axis of the sprocket 38 to the axis of the annular frame 16.

Since the sprockets 37 and 38 also mesh with the corresponding conveyor chains 28 in this embodiment, the anti-corotation mechanism 34 moves in the same direction as the rotation direction of the rotating gantry 1 while rotating on its axis as the rotating gantry 1 rotates. Therefore, this embodiment also provides the same functions and effect offered by the embodiment. Further, since the sprockets 37 and 38 mesh with the conveyor chains 28, provided on the respective inner radial surfaces of the chain attachment portions 15Aa and 16Aa, from inside the conveyor chains 28 in this embodiment, the outer diameters of the ring guide portions 15A and 16A can be made larger than those in the embodiment. Since the guide grooves 56 formed respectively on the ring guide portions 15A and 16A can be expanded outwardly, the moving floor 17 meshes with the ring guide portions 15A and 16A at positions which are spread more outwardly than in the embodiment. This makes it possible to enlarge the therapy gauge 14 in the direction of the radius of the rotary shell 3, thus allowing expansion of the therapy gauge 14 space.

With this embodiment, one of the conveyor chains 28 is indirectly attached to the annular frame 15 via the chain attachment portion 15Aa and the ring guide portion 15A while the other conveyor chain 28 to the annular frame 16 via the chain attachment portion 16Aa and the ring guide portion 16A. However, attachment of the conveyor chains to the annular frames 15 and 16 may be conducted as described below. That is, the guide grooves 56 are formed on the respective side surfaces of the annular frames 15 and 16, and circular grooves wide enough to accommodate the sprockets 37 and 38 are formed more outwardly than those guide grooves 56. The conveyor chains 28 are attached directly to the inner radial surfaces of those circular grooves which face the axis of the rotary shell 3. The sprockets 37 and 38 are slid into their respective circular grooves and made to mesh with the corresponding conveyor chains 28 from inside the conveyor chains 28. This provides the same effect as with this embodiment. Further, it may be possible to attach the cylindrical chain attachment portions to the respective outer radial surfaces of the annular frames 15 and 16 on which the guide grooves are formed and then attach the conveyor chains 28 to the inner radial surfaces of these chain attachment portions. It can be said that each of the configurations discussed above substantially allows meshing of the annular frames 15 and 16 with the sprockets of the anti-corotation mechanism 34 outwardly from the rotation center of the rotating gantry 1.

The sprockets provided on the anti-corotation mechanism mesh with the conveyor chains in each of the embodiments discussed above; however, the present invention is not limited to these embodiments and it may be possible to employ a mesh contact configuration by gears or press contact configuration in which they are engaged with one another by frictional force resulting from the rollers' pressing force. Both of them provide the same effect.

Note that although the synchrotron 43 is employed in the above embodiments as ion beam acceleration means, a cyclotron may be used instead. If a cyclotron is used, the preaccelerator 42 is not required and the ion beam emitted from the ion source is introduced into the cyclotron, accelerated by the cyclotron and then emitted to the beam transfer system 49. Further, the ion beam goes through the beam transfer unit 5, after which the patient 8 on the therapy bed 59 is irradiated with the ion beam from the particle irradiation unit 4.

The present invention allows formation of the substantially level access floor by the flexible moving floor regardless of the position of the irradiation unit emitting particle beams. Further, the present invention allows simplification of the apparatus configurations.

While illustrative and presently preferred embodiments of the present invention have been described in detail herein, it is to be understood that the inventive concepts may be otherwise variously embodied and employed and that the appended claims are intended to be construed to include such variations except insofar as limited by the prior art.

What is claimed is:

1. A medical particle irradiation apparatus comprising:
    a rotating gantry carrying an irradiation unit emitting particle beams;
    a first ring member located within and supported by said rotating gantry such that it can rotate relative to said rotating gantry;
    a second ring member fixedly located across a path of said particle irradiation unit moving in the circumferential direction of said first ring member, from said first ring member;
    a position retaining unit disposed on said rotating gantry, said position retaining unit being in contact with both said first and second ring members to keep the positions of said first and second ring members in the circumferential direction substantially unchanged regardless of the rotation of said rotating gantry;
    a moving floor guide unit disposed on each of said first and second ring members, said moving floor guide unit having a substantially level portion at the bottom; and
    a flexible moving floor located between said first and second ring members, said flexible moving floor moving as said rotating gantry rotates while being guided by the respective moving floor guide units disposed on said first and second ring members, to form therein a therapy room into which a therapy bed is slid,
    wherein said position retaining unit comprises a first rotational element having an uneven portion which meshes with a first uneven portion disposed on said first ring member, a second rotational element having an uneven portion which meshes with a second uneven portion disposed on said second ring member, and a shaft member which couples said first and second rotational elements together, wherein said shaft member is attached to said rotating gantry such that said shaft member is free to rotate on its axis.

2. The medical particle irradiation apparatus according to claim 1, wherein said position retaining unit is attached to said rotating gantry such that it moves in the direction of rotation of said rotating gantry as said rotating gantry rotates and that it can rotate on its axis.

3. The medical particle irradiation apparatus according to claim 2, wherein said position retaining unit comprises a first sprocket which meshes with a first endless link disposed at said first ring member, a second sprocket which meshes with a second endless link disposed at said second ring member, and a shaft member which couples said first and second sprockets together, wherein said shaft member is attached to said rotating gantry such that said shaft member is free to rotate on its axis.

4. The medical particle irradiation apparatus according to claim 1, wherein said position retaining unit is in mesh or press contact with said first and second ring members.

5. The medical particle irradiation apparatus according to claim 4, wherein said position retaining unit is in mesh with said first and second ring members outwardly from the center of rotation of said rotating gantry.

6. The medical particle irradiation apparatus according to claim 1, wherein the distance between the centers of rotation of said first rotational element and of said first ring member is substantially equal to the distance between the centers of rotation of said second rotational element and said second ring member.

7. The medical particle irradiation apparatus according to claim 1, wherein said position retaining unit is disposed on each of a plurality of locations in the circumferential direction of said rotating gantry.

* * * * *